(12) United States Patent
Beitz et al.

(10) Patent No.: US 7,273,646 B2
(45) Date of Patent: Sep. 25, 2007

(54) PERSONAL CARE ABSORBENT ARTICLE HAVING SPLICED ABSORBENT MATERIAL

(75) Inventors: Mark J. Beitz, Appleton, WI (US); Alissa R. Bruss, Appleton, WI (US); Robert J. Makolin, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 69 days.

(21) Appl. No.: 10/768,264

(22) Filed: Jan. 30, 2004

(65) Prior Publication Data

US 2004/0185214 A1 Sep. 23, 2004

Related U.S. Application Data

(62) Division of application No. 10/039,238, filed on Dec. 31, 2001, now Pat. No. 6,863,945.

(51) Int. Cl.
 *B32B 3/00* (2006.01)
(52) U.S. Cl. .................................................. 428/57
(58) Field of Classification Search .................. 428/57
 See application file for complete search history.

(56) References Cited

U.S. PATENT DOCUMENTS

| | | | |
|---|---|---|---|
| 2,428,097 A | 3/1947 | Roslund | |
| 2,495,761 A | 1/1950 | Platt | |
| 2,737,466 A | 3/1956 | Utermohlen, Jr. et al. | |
| 3,633,352 A | 1/1972 | Marriner | |
| 3,664,914 A | 5/1972 | Kubitzek et al. | |
| 3,886,031 A | 5/1975 | Taitel | |
| 4,190,483 A | 2/1980 | Ryan et al. | |
| 4,235,655 A | 11/1980 | DeRoeck et al. | |
| 4,303,712 A | 12/1981 | Woodroof | |
| 4,374,576 A | 2/1983 | Ryan | |
| 4,776,920 A | 10/1988 | Ryan | |
| 4,798,603 A | 1/1989 | Meyer et al. | |
| 4,885,820 A | 12/1989 | Erceg et al. | |
| 4,923,546 A | 5/1990 | Wheeler et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,427,639 A | 6/1995 | Minarelli | |
| 5,482,592 A | 1/1996 | Boriani et al. | |
| 5,509,915 A | 4/1996 | Hanson et al. | |

(Continued)

FOREIGN PATENT DOCUMENTS

DE  19602575 A1  7/1997

(Continued)

*Primary Examiner*—Norca L. Torres Velazquez
(74) *Attorney, Agent, or Firm*—Senniger Powers (57) ABSTRACT

A personal care absorbent article including spliced absorbent material. The absorbent material has a first portion of absorbent material spliced to a second portion of absorbent material to form a longer, continuous length of absorbent material suitable for uninterrupted sequential infeed to a processing machine. A trailing end of the first portion is adjacent a leading end of the second portion. A piece of splicing material is attached to the ends. The piece of splicing material has a fluid permeability at least about as great as a fluid permeability of the first portion of absorbent material and at least about as great as a fluid permeability of the second portion of absorbent material.

23 Claims, 6 Drawing Sheets

U.S. PATENT DOCUMENTS

| | | |
|---|---|---|
| 5,514,237 A | 5/1996 | Emenaker et al. |
| 5,584,897 A | 12/1996 | Christianson et al. |
| 5,601,676 A | 2/1997 | Zimmerman et al. |
| 5,750,217 A | 5/1998 | Kearby et al. |
| 5,968,855 A | 10/1999 | Perdelwitz, Jr. et al. |
| 6,160,197 A | 12/2000 | Lassen et al. |
| 6,255,408 B1 | 7/2001 | Shalaby |
| 6,492,020 B1 | 12/2002 | Ahn et al. |

FOREIGN PATENT DOCUMENTS

| | | |
|---|---|---|
| EP | 0842756 A1 | 5/1998 |
| EP | 0844062 A1 | 5/1998 |
| WO | WO99/59907 | 11/1999 |
| WO | WO 00/77286 A1 | 12/2000 |
| WO | WO 02/102665 A1 | 12/2002 |

PERSONAL CARE ABSORBENT ARTICLE HAVING SPLICED ABSORBENT MATERIAL

CROSS-REFERENCE TO RELATED APPLICATIONS

This application is a divisional of Ser. No. 10/039,238 filed Dec. 31, 2001, now U.S. Pat. No. 6,863,945.

BACKGROUND OF INVENTION

This invention generally relates to the manufacture of absorbent articles from absorbent material, and in particular to a splice connecting two portions of absorbent material which is useable in articles.

Personal care absorbent articles such as disposable diapers, training pants, other infant care products, other child care products, feminine napkins, panty liners, interlabial pads, other feminine care products, incontinence articles, and other adult care products are typically manufactured using high-speed processing machines which convert a stabilized web or ribbon of a fibrous absorbent material into an article. Each web is pre-formed and provided to the machine as a wound roll or coil. To prevent interruption of the processing machine a trailing end of each coil is spliced to a leading end of the next coil. The resulting interconnected web has sufficient tensile strength so that it may be provided to the machine and processed without breaking at the splice.

One drawback to conventional splicing techniques is that the splice is not fluid permeable and therefore unusable in an article. In the past, fibrous absorbent materials have been joined by an adhesive or, since they do not have smooth surfaces which readily hold an adhesive, by an adhesive tape. Adhesives and tape are substantially impermeable to fluid. They hinder fluid from being absorbed by the absorbent structure of the article and degrade effectiveness of the article. As a result, it is necessary to cull all spliced regions of the absorbent material, or to cull all articles that may incorporate a portion of a spliced region, in order to remove all adhesive or tape. In practice, as many as seven articles are culled per splice, producing a costly loss in efficiency and waste of material.

SUMMARY OF THE INVENTION

In general, a process according to the present invention splices a first portion of absorbent material to a second portion of absorbent material to form a longer, continuous length of absorbent material suitable for uninterrupted sequential infeed to a processing machine. The process comprises the steps of placing a trailing end of the first portion adjacent a leading end of the second portion, and aligning the trailing end of the first portion with the leading end of the second portion. A piece of splicing material is attached to the trailing end of the first portion and the leading end of the second portion. The piece of splicing material has a fluid permeability at least about as great as a fluid permeability of the first portion of absorbent material and at least about as great as a fluid permeability of the second portion of absorbent material.

In another aspect, the present invention comprises a continuous length of absorbent material for uninterrupted sequential infeed to a processing machine. The length includes a first portion of absorbent material having a trailing end and a second portion of absorbent material having a leading end adjacent to and aligned with the trailing end of the first portion of absorbent material. A piece of splicing material is attached to the trailing end of the first portion and the leading end of the second portion of absorbent material. The splicing material has a fluid permeability at least about as great as a fluid permeability of the first portion of absorbent material and at least about as great as the second portion of absorbent material.

In yet a further aspect, a personal care absorbent article according to the present invention has a spliced absorbent material. The article comprises a fluid permeable body side liner for placement adjacent a wearer. An absorbent core is attached to the body side liner for absorbing fluid passing through the liner. The absorbent core includes a first portion of absorbent material, a second portion of absorbent material, and a piece of splicing material attached to the first and second portions of absorbent material. The splicing material has a fluid permeability at least about as great as a fluid permeability of the first portion of absorbent material and at least about as great as the second portion of absorbent material.

Other features of the present invention will be in part apparent and in part pointed out hereinafter.

BRIEF DESCRIPTION OF THE DRAWINGS

Corresponding reference characters indicate corresponding parts throughout the views of the drawings.

DETAILED DESCRIPTION OF THE PREFERRED EMBODIMENT

The length of material 20 made according to the present invention is useable in absorbent articles, including, but not limited to, disposable diapers, training pants, other infant care products, other child care products, feminine napkins, panty liners, interlabial pads, other feminine care products, incontinence articles, and other adult care products. Typically, the articles are disposable and not intended for washing and reuse. An exemplary article which may include the length of material described herein is disclosed in U.S. Pat. No. 6,160,197 issued Dec. 12, 2000 to Lassen et al. and entitled "Absorbent Article Having A Body-Accommodating Absorbent Core", which is hereby incorporated by reference. Briefly, the Lassen reference discloses a feminine hygiene product and more particularly a sanitary napkin having a liquid-pervious cover or body side liner, a liquid-impervious baffle or outer cover positioned opposite the body side liner, and an absorbent core positioned between the body side liner and the outer cover.

During manufacture of the absorbent articles, the continuous length of absorbent material 20 is introduced into the processing machine from a suitable supply. For example, the absorbent material may be delivered from a series of supply rolls (not shown), or may optionally be supplied from a upstream inline manufacturing operation.

The first portion of absorbent material 22 has a trailing end 26. The second portion of absorbent material 24 has a leading end 28. Typically, the first and second portions 22, 24 are identical in all respects but they may be different without departing from the scope of the present invention. For example, the second portion 24 may be a different material than the first portion 22.

Figure 1A:
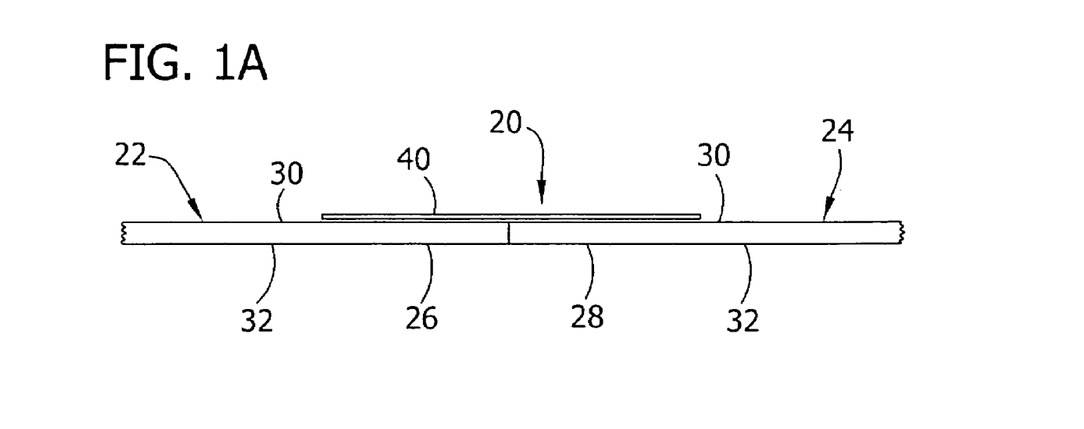
FIG. 1A is a fragmentary schematic elevation of a continuous length of absorbent material of a first embodiment of the present invention.
Figure 1B:
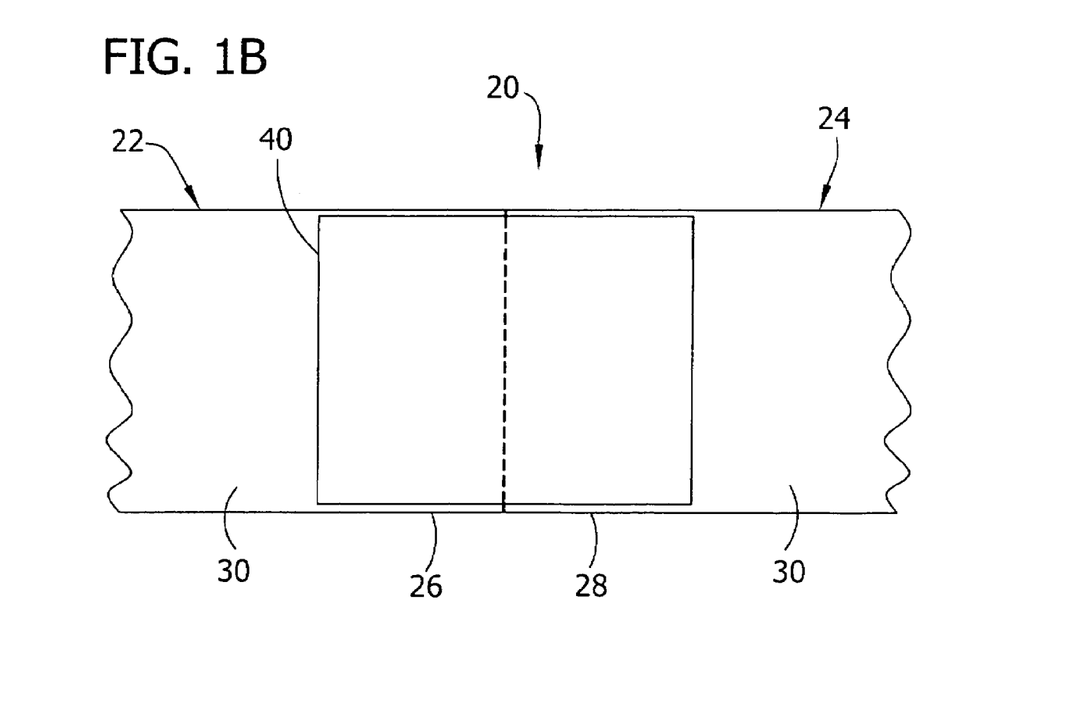
FIG. 1B is a schematic plan of the length of absorbent material shown in FIG. 1A.

The trailing end 26 of the first portion is placed adjacent the leading end 28 of the second portion, and the ends are laterally and vertically aligned as shown in FIGS. 1A and 1B. In the illustrated embodiment, the ends 26, 28 are placed squarely end-to-end as for a conventional butt joint. The ends may be in engagement, or may be spaced apart by a small gap between the ends. The placing of the ends 26, 28 at these positions may be done manually, or by automated machine. An end-to-end arrangement results in better product comfort than an arrangement with the ends overlapped because it is thinner and less bulky. Each of the portions 22, 24 has a first face 30 and an opposite second face 32. The respective first faces 30 of the first and second portions 22, 24 are oriented in an identical direction (e.g., vertically upward, as shown in the drawings). Similarly, the respective second faces 32 are oriented in an identical direction (e.g., vertically downward). It is understood that the faces 30, 32 may be oriented in non-identical directions without departing from the scope of this invention.

A piece of splicing material 40 is positioned adjacent the trailing end 26 of the first portion 22 and the leading end 28 of the second portion 24 for attachment thereto. The piece of splicing material 40 engages at least one of the faces 30, 32 of each of the ends. For the arrangement shown in FIGS. 1A and 1B, the piece of splicing material 40 is positioned adjacent the first face 30 of the trailing end 26 of the first portion and the first face 30 of the leading end 28 of the second portion.

The relative sizes of the materials may vary. Preferably, the piece of splicing material 40 is slightly narrower than the first and second portions 22, 24 of absorbent material so that it does not extend beyond the lateral sides of the material, but yet covers a sufficient shear area to produce an effectively strong splice. The piece of splicing material 40 should overlap each portion of absorbent material in the longitudinal direction by a length sufficient to form a strong splice. For example, portions 22, 24 of absorbent material having a width of about 37 mm may be joined by splicing material having a longitudinal overlap of at least about 25 mm per end (producing a total length of splice of about 50 mm), and more desirably a longitudinal overlap of at least about 50 mm.

In one embodiment, the piece of splicing material 40 is attached to the respective ends 26, 28 of the first and second portions of absorbent material by compressing the arrangement and applying heat energy. The attachment is made using a compression device (not shown), such as a press, anvil, or set of plates which are pressed together. The heat may originate from either a surface source (such as a heated compression device) or from a hot air source such as a through-air bonding technique. The applications of heat and pressure occur simultaneously for a period of time so that the splicing material and/or a binding agent of the absorbent material soften or begin to melt and bind together upon cooling. As these techniques are conventional and well understood by those of ordinary skill in the art, they will not be discussed in further detail.

Significantly, the piece of splicing material 40 is at least as fluid permeable as the first and second portions 22, 24 of absorbent material. Therefore, the splice will not hinder passage of fluid to the absorbent material when incorporated into an article. Further, the splicing material has a tensile strength at least as great as a tensile strength of the absorbent material so that the splice is strong and will not rupture when processed into an article.

The first and second portions 22, 24 of absorbent material may include cellulosic fibers (e.g., wood pulp fibers), other natural fibers, synthetic fibers, superabsorbent material in the form of particles or fibers, binder materials, surfactants, selected hydrophobic materials, or the like, PET fiber, bicomponent fiber, latex, as well as combinations thereof, and other materials suitable to improve absorbent performance and/or web processing. Desirably, the stabilized absorbent material has between 2% and 50% polymer content by weight.

Stabilized absorbent is typically a material capable of retaining fluid to a saturated capacity of at least about 3 g/g and about 10 g of fluid per 0.1 square meter of material as measured by a 0.5 psi saturated capacity test method. Further, the material holds together when dry or at any level of fluid saturation. Dry tensile properties of the material is typically in the range of 0.1–60 kg per cm of material width. Example materials include an airlaid absorbent bonded with a thermally bondable fiber (e.g., bicomponent sheath/core fibers such as KoSa T-255 or Chisso ESC fibers), an airlaid absorbent bonded with dried latex, airlaid absorbents bonded by hydrogen bonding, and wetlaid absorbents.

The absorbent materials are typically formed by employing conventional airlaying techniques, as known in the art. For example, it is common to utilize a fibrous sheet of cellulosic or other suitable absorbent material which is fiberized in a conventional fiberizer, or other shredding or comminuting device, to form discrete fibers. In addition, particles of superabsorbent material are mixed with the discrete fibers. The fibers and superabsorbent particles are then entrained in an air stream and directed to a foraminous forming surface upon which the fibers and superabsorbent particles are deposited to form a fibrous web of absorbent material. In addition, bonding agents or other strengthening components may be incorporated to provide a stabilized web. The web of absorbent material may then be stored or immediately directed for further processing and assembly with other components to produce a final absorbent article.

Other techniques are also employed to form stabilized absorbent webs. Such techniques include: dry-forming techniques, wet-laying techniques, foam-forming techniques, and various wet-forming techniques. The resulting absorbent webs have included absorbent fibers, natural fibers, synthetic fibers, superabsorbent materials, binders, and strengthening components in desired combinations. The stabilized webs may be employed to generate preformed absorbent sheets or layers, and the preformed material may be stored in a preformed supply, such as provided by a supply roll. At an appropriate time, the preformed layer may be delivered from the preformed supply into a manufacturing line.

Suitable stabilized absorbents containing superabsorbent powders for urine absorbing applications typically have a basis weight in the range of about 200–1000 gsm and a web density of about 0.05–0.35 g/cm3. Suitable stabilized airlaid absorbents not containing superabsorbent powders for feminine hygiene or other applications typically have a basis weight in the range of about 100–500 gsm and a web density of about 0.05–0.25 g/cm3. The low density and high basis weight of these materials cause lower than desired roll lengths, forcing the need for a more than desirable number of splices.

Superabsorbent materials are well known in the art, and are readily available from various suppliers. For example, FAVOR 880 superabsorbent is available from Stockhausen, Inc., a business having offices located in Greensboro, N.C., U.S.A.; and DOW 2035 is available from Dow Chemical Company, a business having offices located in Midland, Mich., U.S.A. In one embodiment of the invention, the absorbent material of the portions 22, 24 has an absorbent capacity of at least about 9 g/g employing 0.9 wt % saline (9 grams of 0.9 wt % saline per gram of absorbent material). It has a tensile strength value of at least about 1.7 N/cm (Newtons per cm of "width", of the material, where the "width", direction is perpendicular to the applied force). However, the web of absorbent material can be provided with a tensile strength value of up to about 100 N/cm, or more.

Desirably, the splicing material of the piece 40 is melt compatible with the binder fiber of the absorbent material. One type of splicing material is a carded web comprising bicomponent fibers used to stabilize absorbent structures. Other polymer options for splicing material include polyethylene, polypropylene, other polyolefins. A web comprised of a blend of polymer fibers may also provide a splicing material of good quality. For example, a bonded, carded web comprised of a blend of bicomponent and polyester staple fibers may be a useful splicing material. Beyond bonded carded webs, the splicing material may include spunbond, meltdown, SMS, BFDL, hydroentangled nonwovens, and other nonwoven material comprised in part of a polymer compatible with the synthetic binding material providing stability to the absorbent material to be spliced. Alternatively, the splicing material may be adhesively covered to assist the thermal bonding of the stabilized absorbent. Desirably, the splicing material has a very permeable, open structure.

The splicing material should not impede fluid intake. Accordingly, the splicing material is desirably more fluid permeable than the absorbent material(s) being spliced together. Further, it is desirable for the absorbent material with the splicing material attached to be about as permeable as absorbent material without the splicing material attached.

The splicing material is sufficiently strong to be processed through the processing machine. Preferably, the splice material has a tensile strength at least as great as a tensile strength of the absorbent material.

Figure 2A:
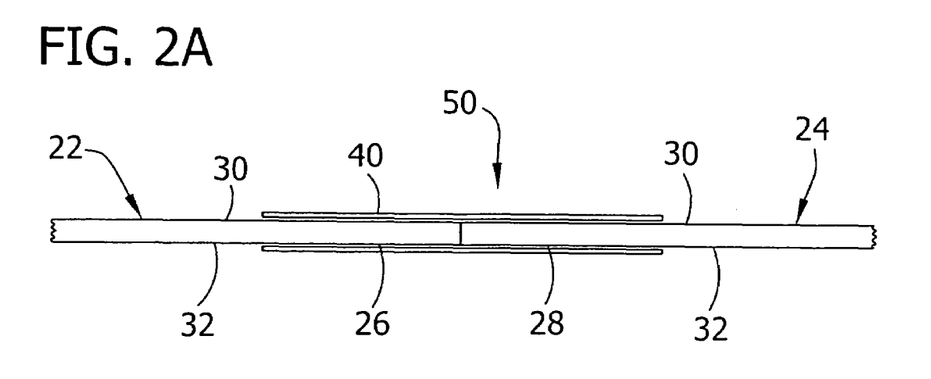
FIGS. 2A and 2B are a schematic elevation and plan, respectively, of a length of absorbent material of a second embodiment.
Figure 2B:
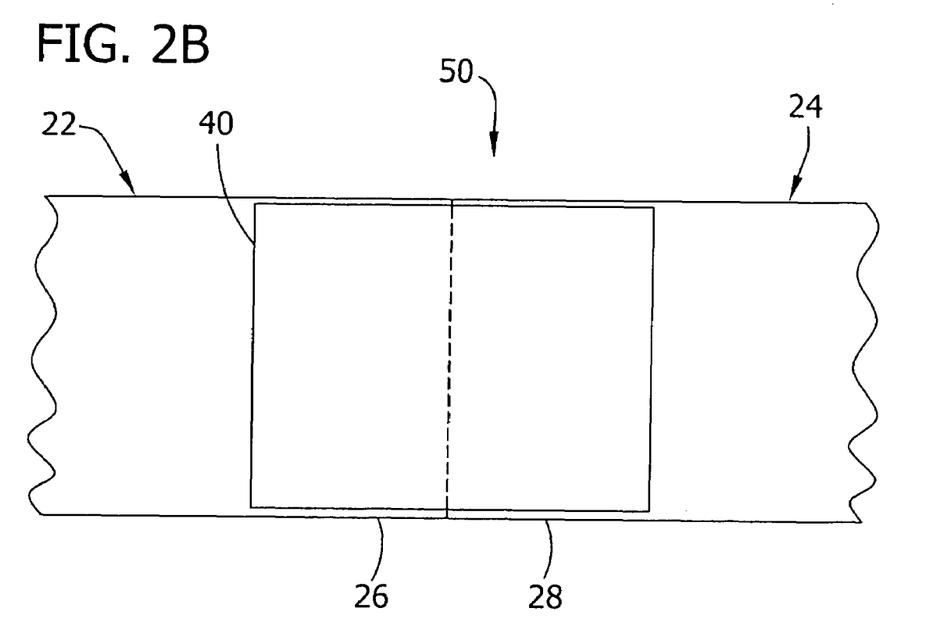

A second embodiment 50 of a continuous length of absorbent material includes two pieces of splicing material 40 on opposite faces of the ends is shown in FIGS. 2A and 2B. A second piece of splicing material 40 is placed on the second face 32 of the trailing end 26 of the first portion of absorbent material and the second face 32 of the leading end 28 of the second portion of absorbent material. The second embodiment 50 has the advantage of a stronger splice because in provides more shear area and more cross-sectional area of splice material. Alternatively, the second embodiment may permit use of splicing material pieces having narrower widths without reducing the strength of the splice.

Figure 3A:
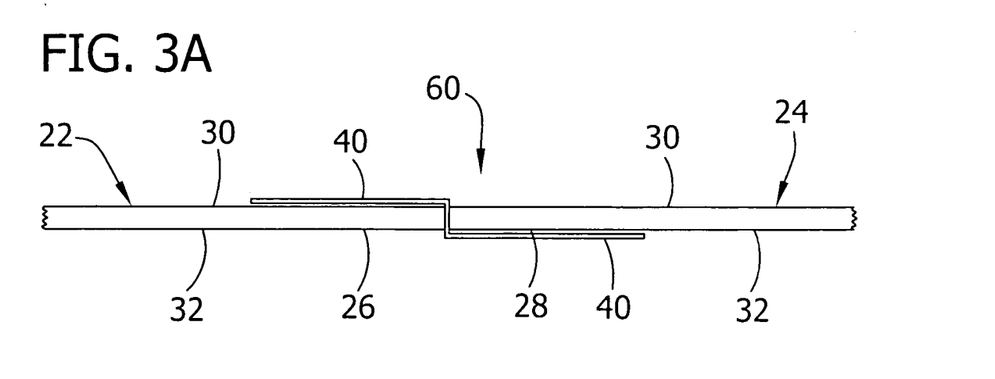
FIGS. 3A and 3B are views similar to FIGS. 1A and 1B of a third embodiment of the present invention.
Figure 3B:
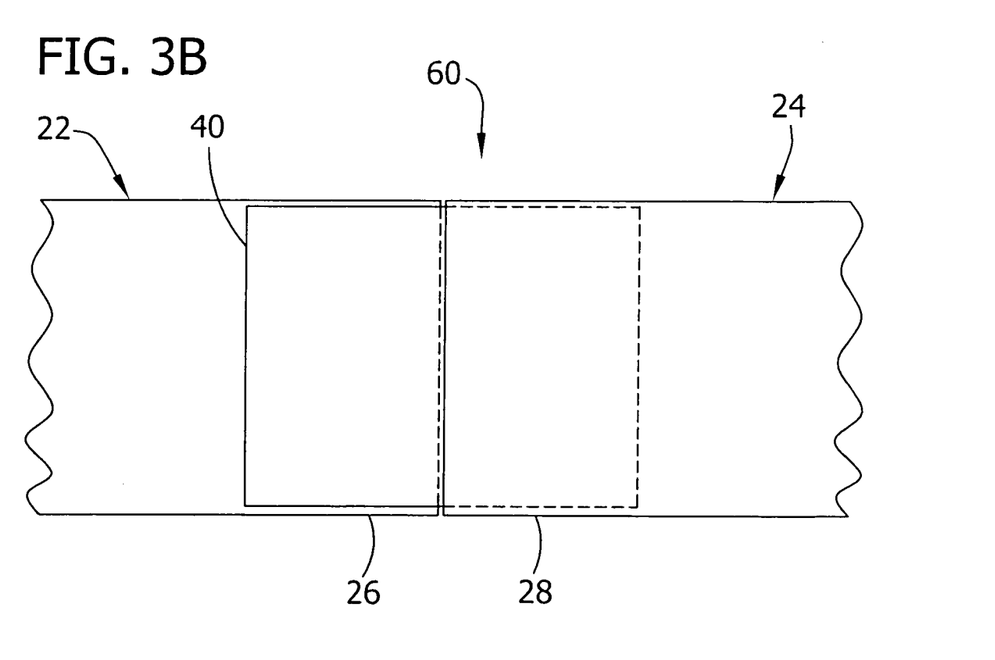

A third embodiment 60 of a continuous length of absorbent material, shown in FIGS. 3A and 3B, places the piece of splicing material 40 on the first face 30 of the trailing end 26 of the first portion and the second face 32 of the leading end 28 of the second portion.

Figure 4A:
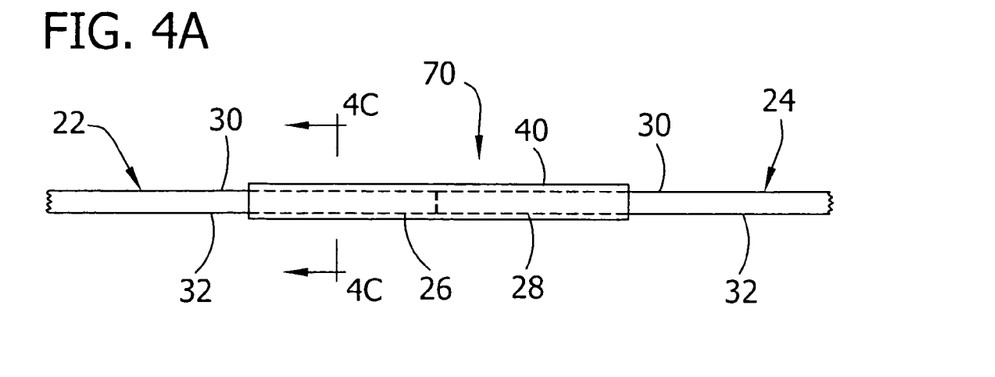
FIGS. 4A and 4B are views similar to FIGS. 1A and 1B of a fourth embodiment of the present invention.
Figure 4B:
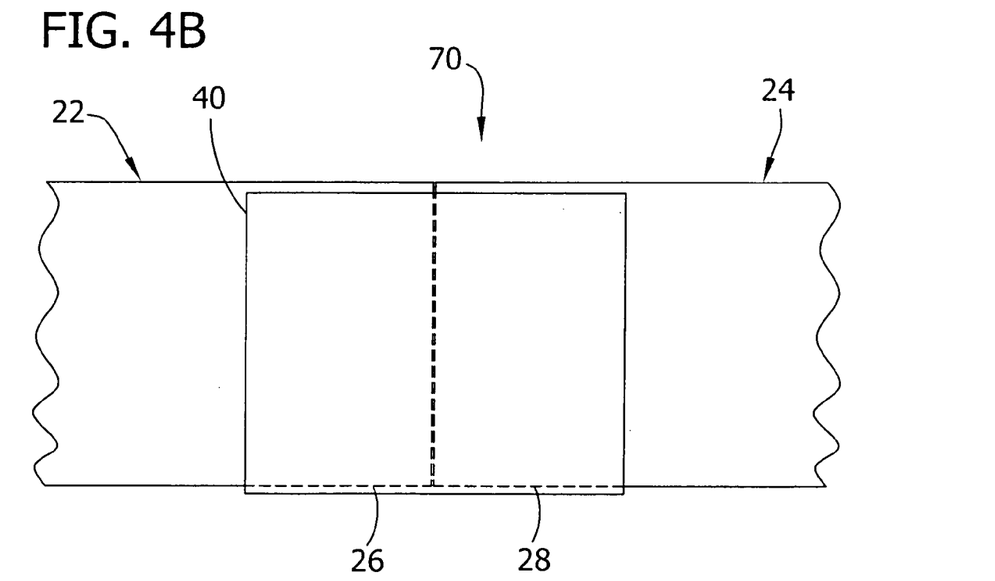
Figure 4C:
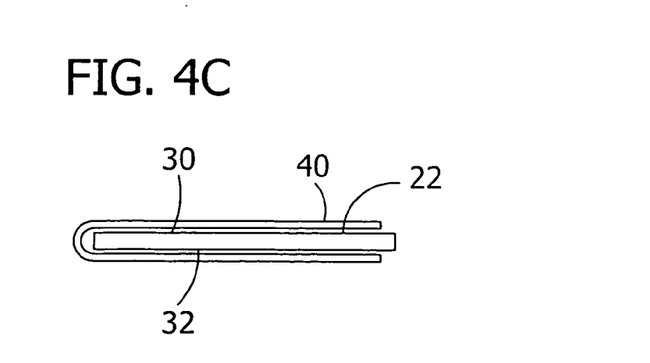
FIG. 4C is a view taken on line 4C—4C of FIG. 4A.

A fourth embodiment 70 of a continuous length of absorbent material, shown in FIGS. 4A, 4B, and 4C, wraps the piece of splicing material 40 around both faces 30, 32 of the ends 26, 28.

Figure 5A:
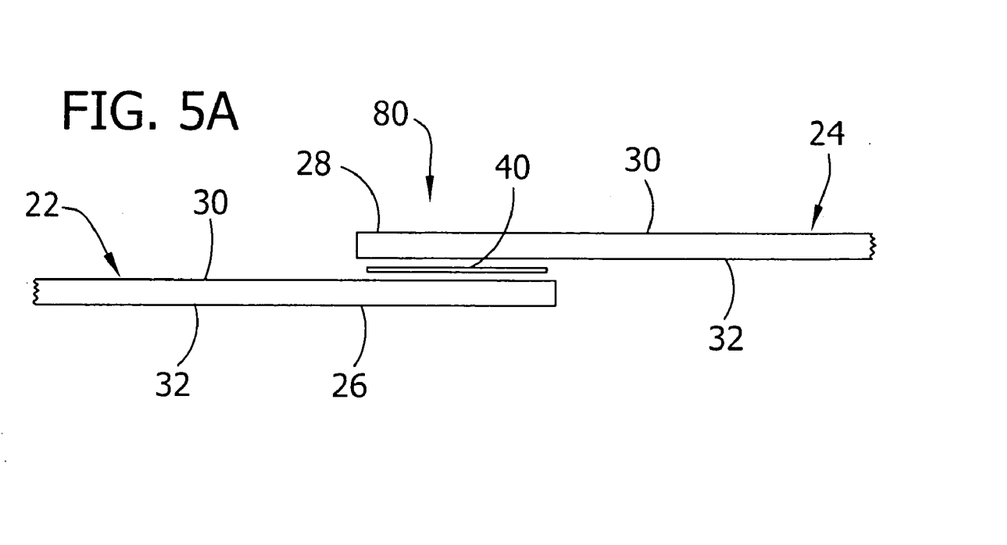
FIGS. 5A and 5B are views similar to FIGS. 1A and 1B of a fifth embodiment of the present invention.
Figure 5B:
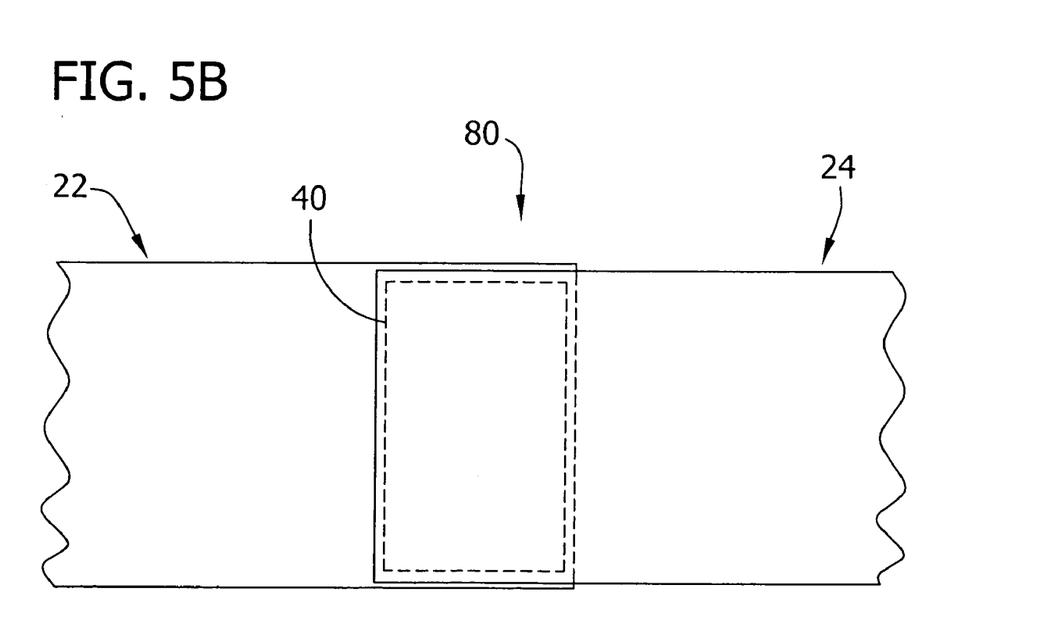
Figure 6:
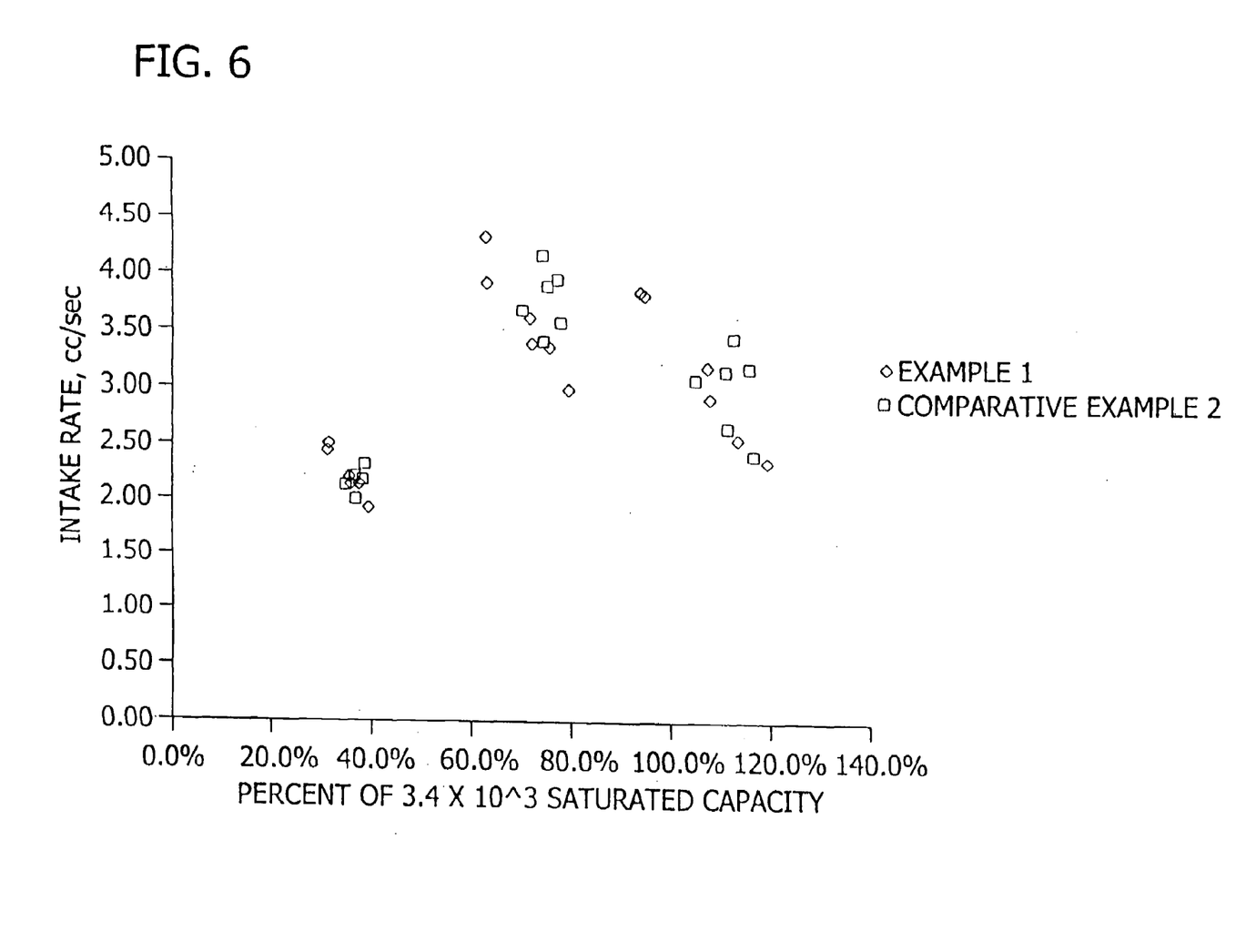
FIG. 6 is a plot of measured fluid intake rate versus percent saturation of 0.9% saline for a representative example of the invention.

A fifth embodiment 80 of a continuous length of absorbent material, shown in FIGS. 5A and 5B, places the piece of splicing material 40 in a sandwiched position between overlapping ends 26, 28 of the first portion and the second portion.

It is understood that other arrangements may be used without departing from the scope of this invention. An adhesive tape may be used in combination with any of these arrangements to further strengthen the splice. However, if such tape is used, it is likely that the manufactured articles containing that tape will need to be culled.

Each end 26, 28 of the portions of absorbent material is shown with generally square, right angles and the piece of splicing material is shown as having a rectangular shape. However, the absorbent material and piece(s) of splicing material 40 may have other shapes and angles without departing from the scope of this invention. Specifically, the ends 26, 28 of the portions of absorbent material may be angled or irregularly shaped, and pieces of splicing material 40 may have an irregular shape or a shape which does not match the shape of the ends. Further, the two ends 26, 28 of the portions of absorbent material need not have corresponding shapes. Gaps between ends 26, 28 may be large and spanned by the piece of splicing material 40.

The present invention is illustrated by the following example which is merely for the purpose of illustration and is not to be regarded as limiting the scope of the invention or the manner in which it is practiced. A thermally bonded airlaid absorbent comprised of about 50% superabsorbent polymer, about 45% fluff pulp, and about 5% of KoSa T-255 Merge 35100A 2.2 dpf bicomponent fiber and having basis weight of about 600 gsm and density of about 0.16 g/cc was cut into two pieces. A through air bonded carded web (TABCW) material comprised of 100% Chisso ESC-HR6 3.0 dpf fiber and having basis weight of about 17 gsm was also cut into two pieces. A Carver Press with capability to heat both top and bottom platens compressed the materials at 1000 psi for six seconds at a temperature of about 135 C. The materials were arranged to form a butt splice as shown in FIGS. 2A and 2B (two pieces of splicing material, one for each face). The resulting splice had favorable bonding strength in the dry state, and continued to hold after the splice was fully swollen in 0.9% saline fluid.

Thus the present invention provides a splice which is strong, dry or wet, and which facilitates a fluid intake equal to that of non-spliced absorbent material. Accordingly, manufactured articles which incorporate the splice need not be culled.

It should be readily apparent that any conventional material may be employed to construct the various components incorporated into the method and apparatus of the invention. Such materials can include synthetic polymers, fiberglass-resin composites, carbon fiber-resin composites, metals, metallic composites, ceramic composites, and the like, as well as combinations thereof. The materials are typically selected to provide desired levels of strength, durability, ease of manufacture, and ease of maintenance. Similarly, in the various attachments and securements employed in the constructions of the method and apparatus of the invention, it should be readily apparent that any conventional attachment or securement technique may be employed.

Although various illustrative and representative configurations have been described in detail herein, it is to be appreciated that other variants, modifications and arrangements are possible. All of such variations, modifications and arrangements are to be considered as being within the scope of the present invention.

In view of the above, it will be seen that the several objects of the invention are achieved and other advantageous results obtained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A personal care absorbent article having a spliced absorbent material, the article comprising:
    a fluid permeable body side liner for placement adjacent a wearer; and
    an absorbent core attached to the body side liner for absorbing fluid passing through the liner, said absorbent core including:
    a first portion of absorbent material;
    a second portion of absorbent material; and
    a piece of splicing material directly attached to said first and second portions of absorbent material, said splicing material having a fluid permeability at least about 25% as great as a fluid permeability of said first portion of absorbent material and at least about 25% as great as said second portion of absorbent material.

2. A personal care absorbent article as set forth in claim 1 wherein said splicing material has a fluid permeability at least about as great as a fluid permeability of said first portion of absorbent material and at least about as great as said second portion of absorbent material.

3. A personal care absorbent article as set forth in claim 2 wherein said article is a feminine hygiene product.

4. A personal care absorbent article as set forth in claim 2 wherein said article is a diaper or training pants for a child.

5. A personal care absorbent article as set forth in claim 2 wherein said article is an incontinence product for an adult.

6. A personal care absorbent article as set forth in claim 2 wherein said first portion comprises a leading end and a trailing end and said second portion comprises a leading end and a trailing end, and wherein said piece of splicing material is thermally bonded to said trailing end of said first portion and to said leading end of said second portion.

7. A personal care absorbent article as set forth in claim 6 wherein said piece of splicing material comprises a carded web of bicomponent fibers.

8. A personal care absorbent article as set forth in claim 1 wherein said first and second portions of absorbent material each include fibers having polyolefin content.

9. A personal care absorbent article as set forth in claim 1 wherein said piece of splicing material is thermally bonding to said first and second portions of absorbent material.

10. A personal care absorbent article as set forth in claim 1 wherein said splicing material is a carded web comprising bicomponent fibers.

11. A personal care absorbent article as set forth in claim 1 wherein said first portion comprises a leading end and a trailing end and said second portion comprises a leading end and a trailing end, and wherein the trailing end of said first portion is arranged squarely end-to-end adjacent the leading end of said second portion.

12. A personal care absorbent article as set forth in claim 1 wherein said first portion comprises a leading end and a trailing end and said second portion comprises a leading end and a trailing end, and wherein said trailing end of said first portion overlaps the leading end of said second portion.

13. A personal care absorbent article as set forth in claim 1 wherein said first portion comprises a leading end and a trailing end and said second portion comprises a leading end and a trailing end, and wherein each of said ends of the first and second portions of absorbent material has a first major surface and an opposite second major surface, and wherein the piece of splicing material comprises is attached to at least one of said first and second major surfaces of each of said ends.

14. A personal care absorbent article as set forth in claim 13 wherein the first surface of the trailing end of the first portion and the first surface of the leading end of the second portion are oriented in an identical direction, and wherein said piece of splicing material is attached to the first surface of the trailing end of the first portion and to the first surface of the leading end of the second portion.

15. A personal care absorbent article as set forth in claim 14 wherein said piece of splicing material is a first piece of splicing material attached to said first surface of the trailing end of the first portion and to said first surface of the leading end of the second portion, further comprising a second piece of splicing material attached to the second surface of the trailing end of the first portion and to the second surface of the leading end of the second portion.

16. A personal care absorbent article as set forth in claim 13 wherein the first surface of the trailing end of the first portion and the first surface of the leading end of the second portion are oriented in an identical direction, and wherein said piece of splicing material is attached to the first surface of the end of the first portion and to the second surface of the end of the second portion.

17. A personal care absorbent article as set forth in claim 13 wherein the piece of splicing material is wrapped around both of said surfaces of each of said ends.

18. A personal care absorbent article as set forth in claim 1 wherein said piece of splicing material includes fibers having polyolefin content.

19. A personal care absorbent article as set forth in claim 18 wherein said piece of splicing material is a nonwoven.

20. A personal care absorbent article as set forth in claim 1 wherein the first portion of the absorbent material is spaced from the second portion of the absorbent material to define a gap therebetween.

21. A personal care absorbent article as set forth in claim 2 wherein said splicing material has a fluid permeability greater than the fluid permeability of said first portion of absorbent material and said second portion of absorbent material.

22. A personal care absorbent article as set forth in claim 16 wherein said splicing material has a generally Z-shape.

23. A personal care absorbent article as set forth in claim 1 wherein the first portion has a trailing end and the second portion has a leading end adjacent to and aligned with the trailing end of the first portion thereby defining an aligned junction of the first and second portions having a length extending generally transverse of the first and second portions, the piece of splicing material being attached to both of the trailing end of the first portion and to the leading end of the second portion of absorbent material such that the splicing material extends continuously over a majority of the length of the aligned junction.

* * * * *